United States Patent [19]

Hood

[11] 4,227,010

[45] Oct. 7, 1980

[54] RECOVERY OF DIMETHYL TEREPHTHALATE AND INTERMEDIATES FROM THE TARRY FRACTION OF COOXIDATION PROCESS RESIDUE

[75] Inventor: Horace E. Hood, Cecil County, Md.

[73] Assignee: Hercofina, Wilmington, N.C.

[21] Appl. No.: 953,228

[22] Filed: Oct. 13, 1978

[51] Int. Cl.$^3$ .............................................. C07C 69/82
[52] U.S. Cl. ........................................ 560/77; 560/78
[58] Field of Search .................................... 560/77, 78

[56] References Cited

U.S. PATENT DOCUMENTS 3,914,287  10/1975  Takeda et al. ......................... 560/77

FOREIGN PATENT DOCUMENTS 73-96541  12/1973  Japan ......................................... 560/77

OTHER PUBLICATIONS

Groggins, Unit Processes in Organic Synthesis, pp. 616–618, (1952).

Primary Examiner—Jane S. Myers

[57] ABSTRACT

Disclosed is a process for recovering dimethyl terephthalate and intermediate products from the tarry fraction of the residue generated in the production of dimethyl terephthalate from p-xylene and methanol by the cooxidation procedure. In the process the tarry fraction is established in admixture with a catalytic quantity of alkali metal material, examples of which are sodium and potassium carbonate, at about 200°–350° C., and the resulting reaction mixture is maintained in this temperature range until at least a substantial quantity of dimethyl terephthalate has formed. Generally, dimethyl terephthalate and intermediate products are separated from the reaction mixture. The separation in preferred embodiments is by distillation.

5 Claims, No Drawings

RECOVERY OF DIMETHYL TEREPHTHALATE AND INTERMEDIATES FROM THE TARRY FRACTION OF COOXIDATION PROCESS RESIDUE

This invention resides in the chemical arts. More particularly, it relates to that branch of organic chemistry having to do with aromatic carboxylic acid esters and processes for making them.

Dimethyl terephthalate (herein "DMT") is a well known chemical of commercial importance. It is used in enormous quantities in the production of polyester polymers from which fibers, film and the like are made.

A classic process for making DMT comprises the steps of oxidizing p-xylene in the liquid state with molecular oxygen to form p-toluic acid, esterifying the acid with methanol to form methyl p-toluate, oxidizing methyl p-toluate with molecular oxygen to form monomethyl terephthalate, and esterifying the monomethyl terephthalate with methanol to form DMT. Oxidation of p-xylene and methyl p-toluate with molecular oxygen is generally effected with an oxidation catalyst such as a heavy metal catalyst, which in preferred embodiments also catalyzes the esterification reactions. Examples of oxidation catalysts disclosed in the art include cobalt or a salt thereof, manganese or a salt thereof, nickel or a salt thereof, both cobalt or a salt thereof and manganese or a salt thereof, both nickel or a salt thereof and manganese or a salt thereof, and the like. This classic process can be carried out on a batch basis or on a continuous basis.

In a preferred practice of the process the oxidation steps are carried out together in an oxidation stage comprising one or more reactors, and the esterification steps are carried out together in an esterification stage comprising one or more reactors. This is referred to herein as the cooxidation-coesterification process. Patents disclosing embodiments of the cooxidation-coesterification process are the U.S. Pat. No. 2,772,305, to Levine et al., and the U.S. Pat. No. 2,894,978, to Katzchmann. See also "Hydrocarbon Processing", November 1975, page 131. In the commercial practice of the cooxidation-coesterification process, which is done on a continuous basis, p-xylene is introduced into the oxidation stage, reaction mixture formed in the oxidation stage, herein referred to as oxidate, is introduced along with methanol into the esterification stage, reaction mixture formed in the esterification stage is removed therefrom and separated by distillation into a distillate comprising DMT and methyl p-toluate, and a residue, and the distillate is separated into a methyl p-toluate fraction and a DMT fraction. The methyl p-toluate fraction is conducted to the oxidation stage. The DMT fraction is treated to obtain DMT of the desired degree of purity. The residue in some instances is cycled to the oxidation stage with only a small proportion thereof being purged from the process. The purged residue is herein called DMT esterified oxidate residue.

DMT esterified oxidate residue comprises a tar-like organic material (herein "tarry fraction") and an oxidation-esterification catalyst fraction. In some cases the catalyst fraction is separated from the tarry fraction, treated to reactivate spent catalyst material, and returned to the oxidation stage. See the U.S. Pat. No. 4,096,340, to Fujii et al.

The prior art has disclosed the heat treatment of the tarry fraction to recover DMT and intermediate (lower boiling) compounds therefrom. The range of temperatures involved in such treatment generally is greater than the range of temperatures actually employed in the oxidation stage. In particular the prior art has disclosed the heat treatment of the tarry fraction in admixture with catalytic quantities of cobalt material (Japanese Published Patent Application No. 48/39457), of manganese material (Japanese Published Patent Application No. 48/96540), of nickel material (Japanese Published Patent Application No. 49/11838), and of titanium material (Japanese Published Patent Application No. 49/36648). Cobalt, manganese, nickel, titanium and compounds thereof are relatively expensive, and, therefore, are not very practical under these conditions.

Hence, a problem to which this invention provides a solution is to provide relative inexpensive material that will promote the formation of DMT in the heat treatment of tarry fraction.

In summary, this invention comprises a process for recovering DMT from the tarry fraction of DMT esterified oxidate residue. The process comprises establishing said residue in admixture with a catalytic quantity of alkali metal material within the temperature range from about 250° to about 350° C., and maintaining the resulting reaction mixture in said temperature range for a period of time sufficient for formation of a substantial quantity of DMT. In most embodiments of the process of the invention, the thus formed DMT is removed from the reaction mixture.

In some embodiments of the invention, the feed to the process is the purged DMT esterified oxidate residue. In other, preferred embodiments, the feed is the tarry fraction containing material remaining after oxidation-esterification catalyst material has been separated from the residue.

Alkali metal material is material selected from the group consisting of the alkali metals, alkali metal oxides, alkali metal hydroxides, alkali metal carbonates, alkali metal bicarbonates and alkali metal salts of carboxylic acids. Exemplary of the alkali metals are lithium, sodium and potassium. Examples of the oxides, hydroxides, bicarbonates and carbonates are the lithium, sodium and potassium oxides, hydroxides, bicarbonates and carbonates. Examples of the alkali metal salts of carboxylic acids include the lithium, sodium and potassium formates, acetates, propionates, benzoates, toluates, monomethyl terephthalates, and the like. In most embodiments of the invention, the alkali metal material consists of one member of the group with a carbonate, particularly sodium or potassium carbonate, being preferred. In other embodiments of the process, however, two or more members of the group are employed.

The quantity of alkali metal material used in admixture with the tarry fraction is a catalytic quantity. In general it should be sufficient to promote the formation of a substantial amount of DMT, but it should be not in excess of the limit of solubility thereof in the reaction mixture under the reaction conditions. In general satisfactory results are obtained with concentrations which give a total metal or metal equivalent in the range from about 2 parts by weight per million parts by weight of the tarry fraction to about 2% by weight of the tarry fraction, with the preferred range being from about 0.05 to about 0.2% by weight of the tarry fraction.

The pressure under which the reaction mixture is established can range from subatmospheric pressure through atmospheric pressure to superatmospheric pressure. However, it is preferred that the reaction mixture be established and maintained under conditions which cause the removal of DMT from the reaction mixture as it is formed. This favors the maximum recovery of DMT from the tarry fraction. While this can be done at atmospheric and superatmospheric pressures by bubbling air or an inert gas (for example, nitrogen) through the reaction mixture throughout most, if not all, of the reaction period, DMT being volatilized in the reaction temperature range, it preferably is accomplished by establishing and maintaining the reaction mixture under subatmospheric pressure throughout most, if not all, of the reaction period. In either case DMT is removed as an overhead or gaseous product. In preferred embodiments the ambient pressure is established and maintained during the reaction period at about 10–200 millimeters of mercury.

The reaction period or amount of time in which the reaction mixture is maintained in the temperature range can vary over a wide range. However, a period of time from about 0.2 to about 48 hours with about 2–18 hours being preferred gives satisfactory results.

The process of this invention can be practiced on a batch basis or on a continuous basis. Preferably, it is practiced on a continuous basis.

In the practice of the process of this invention, not only is DMT formed, but also intermediate products (monomethyl terephthalate, methyl p-toluate, and the like) which in general have lower boiling points than DMT. They generally are recovered with the DMT. Consequently, the gaseous product obtained in the preferred practice of the process of this invention generally is condensed to a liquid and introduced with the feed to the methyl p-toluate/DMT separation step in the cooxidation-coesterification process or charged to some other DMT separation and purification step in the cooxidation-coesterification process. The resinous material that remains after separation of the recovered DMT and intermediate products from the treated tarry fraction is purged from the process in most embodiments of this invention.

This invention and the best mode now contemplated of carrying it out are illustrated by the following working examples in which "w" means parts by weight, "v" means parts by volume, and w is to v as the kilogram is to the liter. This invention is not limited to these working examples.

EXAMPLE 1

This example illustrates a batch mode embodiment of the process of this invention in which the alkali metal material consists essentially of potassium carbonate.

A quantity (1000 w) of DMT esterified oxidate residue from a commercial DMT plant based on the cooxidation-coesterification process and previously treated by an aqueous extraction procedure to separate oxidation-esterification catalyst material therefrom, and a catalytic quantity (1.767 w) of anhydrous potassium carbonate are introduced into the pot of a distillation column having an overhead condenser and vacuum line. The resulting reaction mixture is heated to 290° C. When the temperature of the reaction mixture reaches 150°–200° C., the ambient pressure is reduced to and maintained at 45 millimeters of mercury pressure. If bumping of the reaction mixture during the reaction period is a problem, a tiny stream of air bubbles may be passed through the pot contents by means of a gas inlet tube having an outlet below the reaction mixture level in the pot. The reaction mixture is maintained at this pressure and temperature for about 18.5 hours. During this period of time distillate is condensed and collected. At the end of the reaction period, a substantial quantity (487 w) of distillate will be obtained. A typical analysis of the distillate is: DMT=70.0% by weight, and monomethyl terephthalate 0.8% by weight.

EXAMPLE 2

This example illustrates another batch mode embodiment of the process of this invention in which the alkali metal material consists essentially of sodium carbonate.

A quantity (1000 w) of DMT esterified oxidate residue from a commercial plant based on the cooxidation-coesterification process, which residue has not been treated to remove oxidation-esterification catalyst material and which oxidation-esterification catalyst material comprises a cobalt compound, and a catalytic quantity (2.304 w) of anhydrous sodium carbonate are introduced into the pot of a distillation column having an overhead condenser and vacuum line. The resulting reaction mixture in the pot is heated to about 290° C. When the temperature of the reaction mixture reaches 150°–200° C., the ambient pressure is reduced to and held at about 45 millimeters of mercury. If bumping of the reaction mixture during the reaction period is a problem, a tiny stream of bubbles of air may be passed through the reaction mixture by means of an air pipe with the outlet thereof below the level of the reaction mixture in the pot. The reaction mixture is maintained at this pressure and temperature for the reaction period of 20.0 hours, while distillate is condensed and collected. At the end of the reaction period, a substantial quantity (488 w) of distillate will have accumulated. A typical analysis of the collected distillate is: DMT=60.1% by weight, and monomethyl terephthalate=1.1% by weight.

EXAMPLE 3

This example illustrates another batch mode embodiment of the process of this invention, but one in which the alkali metal material consists essentially of sodium carbonate.

A quantity (1000 w) of DMT esterified oxidate residue from a commercial DMT plant based on the cooxidation-coesterification process and previously treated by an aqueous procedure to remove oxidation-esterification catalyst material therefrom, and a catalytic quantity (2.304 w) of anhydrous sodium carbonate are charged to the pot of a distillation column having an overhead condenser and a vacuum line. The resulting reaction mixture is heated to a temperature of about 290° C. When the temperature of the pot contents reaches 150°–200° C., the ambient pressure of the pot contents is reduced to about 45 millimeters of mercury. If bumping in the pot becomes a problem, a tiny stream of air bubbles may be introduced into the contents by way of an air pipe with the outlet thereof below the level of the reaction mixture. The reaction mixture is maintained at this temperature and ambient pressure for 27.0 hours during which reaction period distillate is condensed and collected. At the end of this reaction period, a substantial quantity (508 w) of distillate will be obtained. A typical analysis of the distillate is: DMT=67.4% by weight and monomethyl terephthalate=0.84% by weight.

EXAMPLE 4

This example illustrates a continuous mode embodiment of the process of this invention in which the alkali metal material consists essentially of sodium carbonate.

A stream (100 v per minute) containing tarry fraction and resulting from the treatment by an aqueous extraction procedure to remove oxidation-esterification catalyst material, of a typical DMT esterified oxidate residue stream from a commercial DMT plant based on the cooxidation-coesterification process is introduced into a mixing tank along with a catalytic quantity (0.11 w per minute) of anhydrous sodium carbonate. Resulting mixture is introduced into a falling film evaporator to remove residual water from the extraction procedure. A stream (83.6 v per minute) from the bottom of the falling film evaporator is fed into a feed tank.

A stream (127.4 v. per minute; density=1155 kilograms per cubic meter) is conducted from the feed tank into a first fractional distillation column having an overhead condenser with a condensate collection tank, and a vacuum line. The pressure at the top of the column is about 50 millimeters of mercury while the temperature at the bottom of the first distillation column is established and maintained at about 280° C.

A stream (95.6 v per minute) from the bottom of the first distillation column is introduced into a second fractional distillation column having an overhead condenser and condensate collection tank, and a vacuum line. The temperature at the bottom of the second fractional distillation column is established and maintained at about 290° C., while the pressure at the top of the second fractional distillation column is maintained at about 20 millimeters of mercury.

A stream (43.8 v per minute) of second fractional distillation column condensate is removed from the second fractional distillation column condensate tank and passed to the first distillation column feed tank. The second distillation column has a bottoms stream (51.8 v per minute) as the purge stream of the process.

A stream (31.8 v per minute) is removed from the first fractional distillation column condensate collection tank with recovered DMT stream. A typicl analysis ot this stream is: DMT=71.2% by weight.

Results similar to those of the foregoing working examples are obtained with other members of the group consisting of alkali metals and alkali metal oxides, hydroxides, bicarbonates, carbonates and salts of carboxylic acids.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

The expression "consisting essentially of" as used in this specification excludes any unrecited substance at a concentration sufficient to substantially adversely affect the essential properties and characteristics of the composition of matter being defined, while permitting the presence of one or more unrecited substances at concentrations insufficient to substantially adversely affect said essential properties and characteristics.

We claim:

1. In a process for the heat treatment of the tarry fraction of DMT esterified oxidate residue to recover dimethyl terephthalate therefrom, the improvement wherein said tarry fraction, substantially free of water and of oxidation-esterification catalyst material, is established in admixture with a catalytic quantity of alkali metal material within the temperature range from about 250° to about 350° C., and the resulting reaction mixture is maintained in said temperature range for a period of time sufficient for formation of a substantial quantity of dimethyl terephthalate.

2. The process of claim 1 in which said resulting reaction mixture is established in said temperature range under 10–200 millimeters of mercury pressure, and maintained thereat for a period of about 0.2 to about 48 hours.

3. The process of claim 2 in which said quantity is such as to provide a total alkali metal or alkali metal equivalent in the range from about 2 parts by weight per million parts by weight of the tarry fraction to about 2% by weight of the tarry fraction.

4. The process according to claim 3 in which the alkali metal material consists essentially of sodium carbonate.

5. The process according to claim 3 in which the alkali metal material consists essentially of potassium carbonate.

* * * * *